United States Patent
Hagi et al.

(10) Patent No.: US 12,086,991 B2
(45) Date of Patent: Sep. 10, 2024

(54) SYSTEM AND METHOD FOR IMAGE SYNTHESIS OF DENTAL ANATOMY TRANSFORMATION

(71) Applicant: Tasty Tech Ltd., Toronto (CA)

(72) Inventors: Gil Hagi, Toronto (CA); Balazs Keszthelyi, Budapest (HU)

(73) Assignee: Tasty Tech Ltd., Toronto (CA)

( * ) Notice: Subject to any disclaimer, the term of this patent is extended or adjusted under 35 U.S.C. 154(b) by 397 days.

(21) Appl. No.: 17/539,386

(22) Filed: Dec. 1, 2021

(65) Prior Publication Data

US 2022/0180527 A1  Jun. 9, 2022

Related U.S. Application Data

(60) Provisional application No. 63/199,038, filed on Dec. 3, 2020.

(51) Int. Cl.
*G06N 3/0455* (2023.01)
*A61C 13/00* (2006.01)
(Continued)

(52) U.S. Cl.
CPC .......... *G06T 7/168* (2017.01); *A61C 13/0004* (2013.01); *G06N 3/0455* (2023.01);
(Continued)

(58) Field of Classification Search
CPC .......... G06N 3/045; G06N 20/00; G06N 3/02; G06N 3/09; G06N 5/04; G06N 3/0475; G06N 3/0455; G06N 3/0895; G06N 3/08; G06V 10/82; G06V 10/7784; G06V 10/70; G06V 40/174; G06V 40/168; G06V 40/16; G06V 10/26; G06V 20/70; G06V 10/762;
(Continued)

(56) References Cited

U.S. PATENT DOCUMENTS

2022/0148188 A1* 5/2022 Hagi .................. G06T 7/11

OTHER PUBLICATIONS

Hao et al., Clinically Applicable System For 3D Teeth Segmentation in Intraoral Scans using Deep Learning, posted: Nov. 10, 2020 [retrieved Mar. 19, 2024], version 1, 22 pages. Retrieved: https://www.researchsquare.com/article/rs-103285/v1 (Year: 2020).*

(Continued)

*Primary Examiner* — Matthew C Bella
*Assistant Examiner* — Dennis Rosario
(74) *Attorney, Agent, or Firm* — Marks & Clerk

(57) ABSTRACT

Provided is a system and a method for image synthesis of dental anatomy transformation. In an aspect, there is provided a method including: receiving an input image, the input image including a mouth with teeth exposed; building an input segmentation map using the input image as input to an artificial neural network; transforming the input segmentation map into an input latent vector using a trained encoder; transforming the input latent vector to an output latent vector using a trained transformer machine learning model; transforming the output latent vector to an output segmentation map using a trained decoder; generating a simulated image using the output segmentation map as input to a generative adversarial network; and outputting the simulated image, the output segmentation map, or both.

23 Claims, 6 Drawing Sheets

(51) Int. Cl.
*G06T 7/11* (2017.01)
*G06T 7/168* (2017.01)
*G06V 10/82* (2022.01)
*A61B 5/00* (2006.01)
*A61B 6/51* (2024.01)

(52) U.S. Cl.
CPC ................ *G06T 7/11* (2017.01); *G06V 10/82* (2022.01); *A61B 5/4547* (2013.01); *A61B 6/51* (2024.01); *G06T 2207/20081* (2013.01); *G06T 2207/30036* (2013.01)

(58) Field of Classification Search
CPC ........... G06V 2201/033; G06V 40/175; G06V 40/176; G06V 2201/03; G06V 40/165; G06V 40/167; G06T 2207/20081; G06T 2207/20084; G06T 2207/30036; G06T 7/11; G06T 7/10; G06T 7/12; G06T 5/60; G06T 9/002; G06T 3/4046; G06T 9/00; G06T 2207/30008; G06T 2219/004; G06T 7/168; G06T 7/0012; G06T 2210/41; A61B 5/0088; A61B 5/7267; A61B 6/5294; A61B 6/512; A61B 6/51; A61B 5/4547; A61B 5/7425; A61B 5/4552; A61B 5/4557; A61B 5/4542; G16H 30/40
See application file for complete search history.

(56) References Cited

OTHER PUBLICATIONS

Wang et al., Learning How to Smile: Expression Video Generation With Conditional Adversarial Recurrent Nets, 1st public instance: Jan. 1, 2020 [retrieved Mar. 19, 2024], IEEE Transactions on Multimedia, vol. 22, Issue: 11, Nov. 2020, pp. 2808-2819. Retrieved: (Year: 2020) https://ieeexplore.ieee.org/abstract/document/8948254 (Year: 2020).*

Zanjani et al., Mask-MCNet: Instance Segmentation in 3D Point Cloud of Intra-oral Scans, Oct. 10, 2019 [retrieved Mar. 19, 2024], Medical Image Computing and Computer Assisted Intervention—MICCAI 2019, Lecture Notes in Computer Science: vol. 11768 , pp. 128-139. Retrieved: (Year: 2019) https://link.springer.com/chapter/10.1007/978-3-030-32254-0_15 (Year: 2019).*

Yang et al., iOrthoPredictor: model-guided deep prediction of teeth alignment, Jan. 12, 2020 [retrieved Jun. 15, 2024], ACM Transactions on Graphics, vol. 39, No. 6, Article 1, 16 pages. Retrieved: https://scholars.cityu.edu.hk/en/publications/publication(71e86577-d47e-4512-9bb7-0570f67d15b7).html (Year: 2020).*

* cited by examiner

SYSTEM AND METHOD FOR IMAGE SYNTHESIS OF DENTAL ANATOMY TRANSFORMATION

CROSS-REFERENCE TO RELATED APPLICATION

This application claims the benefit of United Stated Provisional Patent Application No. 63/199,038 filed on Dec. 3, 2020, which is each hereby incorporated herein by reference.

TECHNICAL FIELD

The following relates generally to imaging manipulation using machine learning techniques; and more specifically to a system and method for automated simulation of teeth transformation.

BACKGROUND

When communicating dental procedures to patients, especially those that relate to cosmetic dentistry, dentists often have to revert to describing or drawing the results of the procedure, or having to provide a picture of an unrelated person to illustrate the results of the procedure. Such approach is generally disadvantageous because the descriptions and drawings are often crude, or the patient has to use their imagination to effectively fill in the blanks to understand how the results of the procedure will look.

SUMMARY

In at least one broad aspect, in accordance with the teachings herein, there is provided a method for image synthesis of dental anatomy transformation, comprising: generating, from an input image, an input latent vector, wherein the input image comprises a plurality of pixels and at least a subset of pixels, of the plurality of pixels, corresponds to one or more exposed teeth in a subject's intraoral region, wherein generating of the input latent vector comprises: analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label; and encoding, using a trained encoder model, the input segmentation map to generate the input latent vector, wherein the input latent vector is a compressed representation of the input segmentation map; transforming, using a trained transform model, the input latent vector into an output latent vector; decoding, using a trained decoder, the output latent vector to generate an output segmentation map, the output segmentation map comprising a transformed semantic representation comprising, for one or more teeth, one or more respective transformed groups of pixels; and synthesizing, using a trained synthesis model, the output segmentation map to generate an output simulated image that displays the subject's intraoral region including simulated teeth having the one or more respective transformed groups of pixels.

In some embodiments, the method further comprises generating an output including one or more of the output segmentation map and the output simulated image.

In some embodiments, the teeth, expressed by respective transformed group of pixels, have one or more of a transformed position, transformed orientation or transformed shape.

In some embodiments, a segment of the plurality of pixels, in the input image, corresponds to a region outside of the subject's intraoral region, and analyzing the plurality of pixels to generate the input segmentation map further comprises assigning the segment of pixels to an irrelevancy mask, and the segment of pixels assigned to the irrelevancy mask are excluded from the encoding, transforming and decoding and are included in the output segmentation map to define the location and shape of the intraoral region.

In some embodiments, the trained encoder and trained decoder comprise an auto-encoder.

In some embodiments, the method further comprises training an encoder and a decoder to generate the trained encoder and the trained decoder by: receiving a first segmentation map; encoding, using the encoder, the first segmentation map to generate a latent vector; decoding, using the decoder, the latent vector to generate a second segmentation map; determining a loss function associated with a difference between the first and second segmentation maps; and using the loss function to train the autoencoder.

In some embodiments, each of the trained encoder and trained decoder use a multi-layer perceptron architecture, and wherein the multi-layer-perceptron architecture for the trained encoder can comprise a plurality of expand then squeeze layers each followed by a LeakyRelu activation except for a last layer that is followed by a Tan H function to accommodate for a desired type of latent vector.

In some embodiments, the trained encoder and trained decoder use a convolution neural network (CNN), wherein for the trained encoder, the activation functions comprise LeakyRelu activation except for a last convolution layer that is followed by a Tan H function.

In some embodiments, the trained encoder converts the input segmentation map of dimensions L×M×S into the input latent vector of dimensions 1×1×P, wherein "P" is a dimension count of the input latent vector, "L" and "M" are the dimensions of the input image, and "S" is the number of semantic categories, and the input latent vector defines an input tensor, and at one or more layers of the CNN, a resolution of the input tensor is reduced by a factor of 2×2 while concurrently doubling a number of kernels up to "P" kernels to generate the input latent vector of dimensions 1×1×P, and the trained decoder has an inverse structure to the trained encoder and converts the output latent vector having dimensions of 1×1×P to the output segmentation map having dimensions of L×M×S.

In some embodiments, the trained synthesis model comprises a trained conditional generative adversarial network (GAN), the conditional GAN comprises one or more of an encoder, a coarse-to-fine generator, a multi-scale discriminator and a robust adversarial learning objective function and the multi-scale discriminator comprises a plurality of single-scale discriminators having identical or similar structure but operate at different image scales comprising different resolution versions of a same image.

In some embodiments, transforming the input latent vector into the output latent vector further comprises the trained transform model inserting a representation of one or more simulated teeth in the output latent vector.

In another broad aspect, in accordance with the teachings herein, there is provided a system for image synthesis of dental anatomy transformation, comprising: a memory unit for storing an input image, wherein the input image comprises a plurality of pixels and at least a subset of pixels, of the plurality of pixels, corresponds to one or more exposed teeth in a subject's intraoral region; a processing unit coupled to the memory unit and being operable to perform a method comprising: generating, from the input image, an input latent vector, wherein generating of the input latent vector comprises: analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label; encoding, using a trained encoder model, the input segmentation map to generate the input latent vector, wherein the input latent vector is a compressed representation of the input segmentation map; transforming, using a trained transform model, the input latent vector into an output latent vector; decoding, using a trained decoder, the output latent vector to generate an output segmentation map, the output segmentation map comprising a transformed semantic representation comprising, for one or more teeth, one or more respective transformed pixels; and synthesizing, using a trained synthesis model, the output segmentation map to generate an output simulated image that displays the subject's intraoral region including simulated teeth having the one or more respective transformed groups of pixels.

In some embodiments, the processing unit is further operable to preform the method comprising: generating an output including one or more of the output segmentation map and the output simulated image.

In some embodiments, the teeth, expressed by respective transformed group of pixels, have one or more of a transformed position, transformed orientation or transformed shape.

In some embodiments, a segment of the plurality of pixels, in the input image, corresponds to a region outside of the subject's intraoral region, and analyzing the plurality of pixels to generate the input segmentation map further comprises assigning the segment of pixels to an irrelevancy mask, and the segment of pixels assigned to the irrelevancy mask are excluded from the encoding, transforming and decoding and are included in the output segmentation map to define the location and shape of the intraoral region.

In some embodiments, the trained encoder and trained decoder comprise an auto-encoder.

In some embodiments, the processing unit is further operable to preform training of an encoder and a decoder to generate the trained encoder and the trained decoder by: receiving a first segmentation map; encoding, using the encoder, the first segmentation map to generate a latent vector; decoding, using the decoder, the latent vector to generate a second segmentation map; determining a loss function associated with a difference between the first and second segmentation maps; and using the loss function to train the autoencoder.

In some embodiments, each of the trained encoder and trained decoder use a multi-layer perceptron architecture, and wherein the multi-layer-perceptron architecture for the trained encoder can comprise a plurality of expand then squeeze layers each followed by a LeakyRelu activation except for a last layer that is followed by a Tan H function to accommodate for a desired type of latent vector.

In some embodiments, the trained encoder and trained decoder use a convolution neural network (CNN), wherein for the trained encoder, the activation functions comprise LeakyRelu activation except for a last convolution layer that is followed by a Tan H function.

In some embodiments, the trained encoder converts the input segmentation map of dimensions L×M×S into the input latent vector of dimensions 1×1×P, wherein "P" is a dimension count of the input latent vector, "L" and "M" are the dimensions of the input image, and S is the number of semantic categories, and the input latent vector defines an input tensor, and at one or more layers of the CNN, a resolution of the input tensor is reduced by a factor of 2×2 while concurrently doubling a number of kernels up to "P" kernels to generate the input latent vector of dimensions 1×1×P, and the trained decoder has an inverse structure to the trained encoder and converts the output latent vector having dimensions of 1×1×P to the output segmentation map having dimensions of L×M×S.

In some embodiments, the trained synthesis model comprises a trained conditional generative adversarial network (GAN), the conditional GAN comprises one or more of an encoder, a coarse-to-fine generator, a multi-scale discriminator and a robust adversarial learning objective function and the multi-scale discriminator comprises a plurality of single-scale discriminators having identical or similar structure but operate at different image scales comprising different resolution versions of a same image.

In some embodiments, transforming the input latent vector into the output latent vector further comprises the trained transform model inserting a representation of one or more simulated teeth in the output latent vector.

In another broad aspect, in accordance with the teachings herein, there is provided a non-transitory computer-readable medium storing computer program instructions which, when executed by a computer processor, cause the computer processor to perform a method for image synthesis of dental anatomy transformation, the method comprising: generating, from an input image, an input latent vector, wherein the input image comprises a plurality of pixels and at least a subset of pixels, of the plurality of pixels, corresponds to one or more exposed teeth in a subject's intraoral region, wherein generating of the input latent vector comprises: analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label; and encoding, using a trained encoder model, the input segmentation map to generate the input latent vector, wherein the input latent vector is a compressed representation of the input segmentation map; transforming, using a trained transform model, the input latent vector into an output latent vector; decoding, using a trained decoder, the output latent vector to generate an output segmentation map, the output segmentation map comprising a transformed semantic representation comprising, for one or more teeth, one or more respective transformed groups of pixels; and synthesizing, using a trained synthesis model, the output segmentation map to generate an output simulated image that displays the subject's intraoral region including simulated teeth having the one or more respective transformed groups of pixels.

These and other embodiments are contemplated and described herein. It will be appreciated that the foregoing summary sets out representative aspects to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

Figure 1:
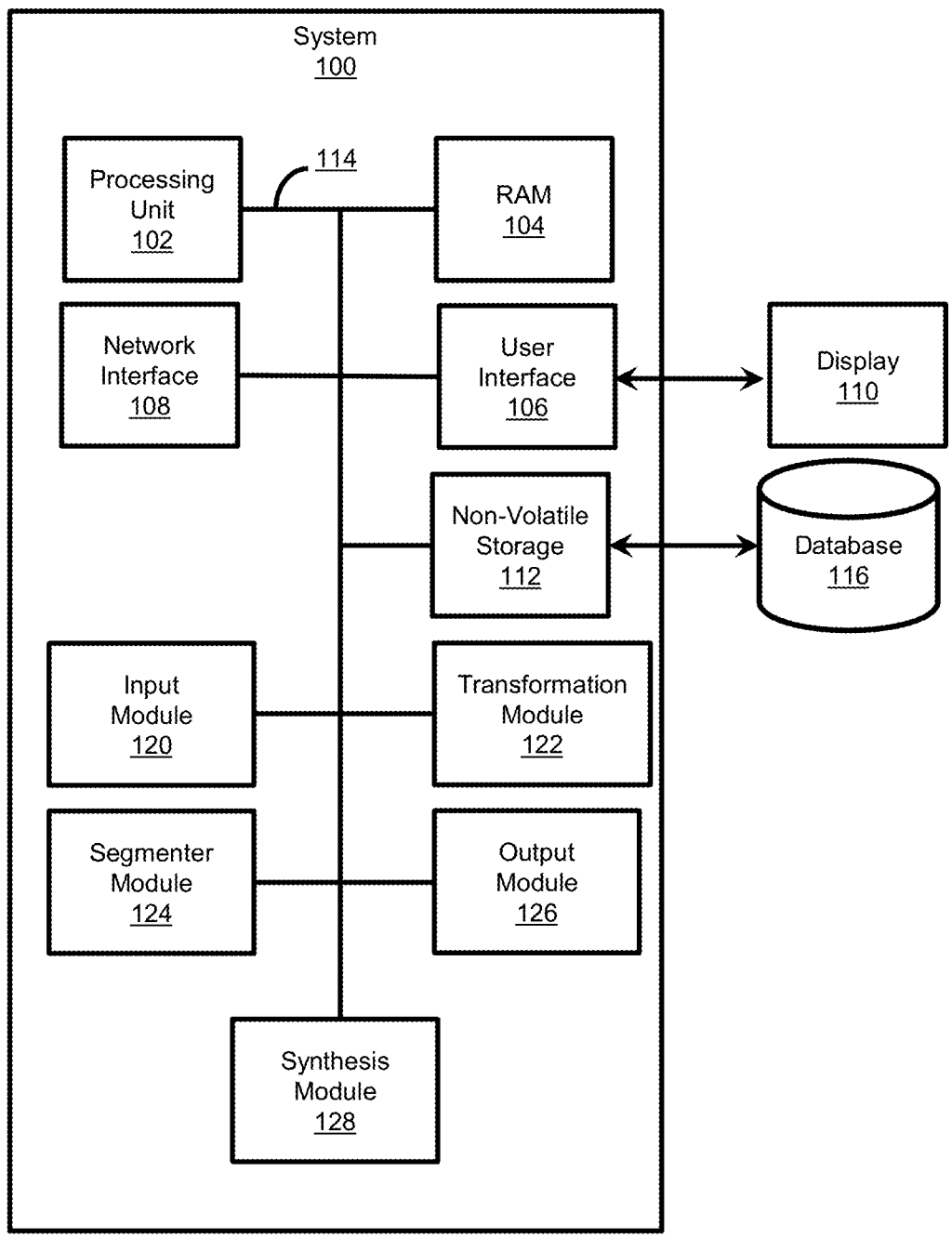
FIG. 1 is a schematic diagram of a system for image synthesis of dental anatomy transformation, in accordance with an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Both shared memory and distributed memory systems are possible, for example in ways that would rely on discrete accelerators cards (GPU, FPGA, ASIC) with their own memory. Any method, application or module herein described may be implemented using computer readable/executable instructions that may be stored or otherwise held by such computer readable media and executed by the one or more processors.

The following relates generally to imaging manipulation using machine learning techniques; and more specifically to a system and method for automated simulation of teeth transformation.

The present embodiments advantageously allow digital images of a patient's mouth (for example, during a smile) to be taken as an input and a simulated version of the patient's mouth after a cosmetic dental procedure to be provided as output. Thus, allowing the patient to fully visualize the result of the procedure and help the dentist convince the patient of the merits of undertaking such procedure. The present embodiments overcome substantial challenges in the art; for example, problems associated with whitening of the teeth and problems related to structure (layout) of the teeth within the intraoral region. The present embodiments use machine learning techniques to overcome at least these problems; for example, determining teeth layout idealization with the use of semantical transformation.

Referring now to FIG. 1, a system 100 for image synthesis of dental anatomy transformation, in accordance with an embodiment, is shown. In this embodiment, the system 100 is run on a local computing device. In further embodiments, the local computing device can have access to content located on a server over a network, such as the Internet. In further embodiments, the system 100 can be run on any suitable computing device, for example, a server. In some embodiments, the components of the system 100 are stored by and executed on a single computer system. In other embodiments, the components of the system 100 are distributed among two or more computer systems that may be locally or remotely distributed.

FIG. 1 shows various physical and logical components of an embodiment of the system 100. As shown, the system 100 has a number of physical and logical components, including a processing unit 102 (comprising one or more processors of possibly different kinds), random access memory ("RAM") 104, a user interface 106, a network interface 108, non-volatile storage 112, and a local bus 114 enabling processing unit 102 to communicate with the other components. In some cases, at least some of the one or more processors can be graphical processing units. Processing unit 102 can execute an operating system, and various modules, as described below in greater detail. The processing unit 102 can execute the modules outside of the context of an operating system. RAM 104 provides relatively responsive volatile storage to processing unit 102 and it may present a single, unified address space as well as distributed memory domains, whilst the physical implementation may also be heterogenous in nature. The user interface 106 enables an administrator or user to provide input via an input device, for example a keyboard and mouse. The user interface 106 also outputs information to output devices for the user, such as to a display 110. The network interface 108 permits communication with other systems, such as other computing devices and servers remotely located from the system 100, such as for a typical cloud-based access model. Non-volatile storage 112 stores the operating system and programs, including computer-executable instructions for implementing the operating system and modules, as well as any data used by these services. Additional stored data can be stored in a database 116. During operation of the system 100, the operating system, the modules, and the related data may be retrieved from the non-volatile storage 112 and placed in RAM 104 to facilitate execution.

In an embodiment, the system 100 further includes a number of functional modules that can be executed on the processing unit 102; for example, an input module 118, a transformation module 120, a segmenter module 124, a synthesis module 128, and an output module 126. In some cases, the functions and/or operations of the modules can be combined or executed on other modules.

In some embodiments of the system 100, representation of semantics for the teeth in an input image can be accomplished with the use of segmentation maps (SM). The input for the segmentation is a received image comprising a subject's mouth and teeth. The output of the segmentation is an appropriate categorical representation SM of said image. The particular representation can comprise one of one-hot, target encoding, weight of evidence, or other suitable approach. In an example, category zero represents areas outside of the intraoral region (denoted as an irrelevancy_mask, as it signifies the area that may be discarded or excluded from synthesis), while the other categories represent other aspects of the mouth; such as specific teeth and other parts of the intraoral region.

For the case of one-hot representations, two distinct representations can be used. One such representation uses "hard semantics", which is when an integer label is assigned to each pixel with a category label; in this way, it can be stored as a greyscale image. Hard semantics are equivalent to a vector(s) where all values are zeros, except the value under a given category index, which is one. The other representation uses "soft semantics". Soft semantics are a similarly sized vector(s), albeit more relaxed, where the sum of its values is one. However, none of the particular values are constrained to be zero or one as they can be any value between zero and one as long as the sum is equal to one. The soft semantics advantageously allows for the representation of transitions from one category to another in a smooth manner, making interpolation possible between the values.

In an example, the SMs can be H×W×S tensors; where H is the height of the input image, W is the width of the input image, and S is the number of semantical categories (for example, 256×256×31). In some cases, the semantical categories can use a one-hot encoding map; however, any suitable encoding can be used. In an example, a one-hot categorization can be assigned for each tooth position and for each item in the mouth (for example, tongue). In this example, using soft semantics, every (x, y) location in the SM corresponds to an S-wide vector that is sums up to '1'. More specifically, all elements of the vector are [0.0, 1.0] real numbers where:

$$\Sigma_{s=0,x=0,y=0}^{S-1,M-1,N-1} SM(x,y,s)=1$$

Figure 2:
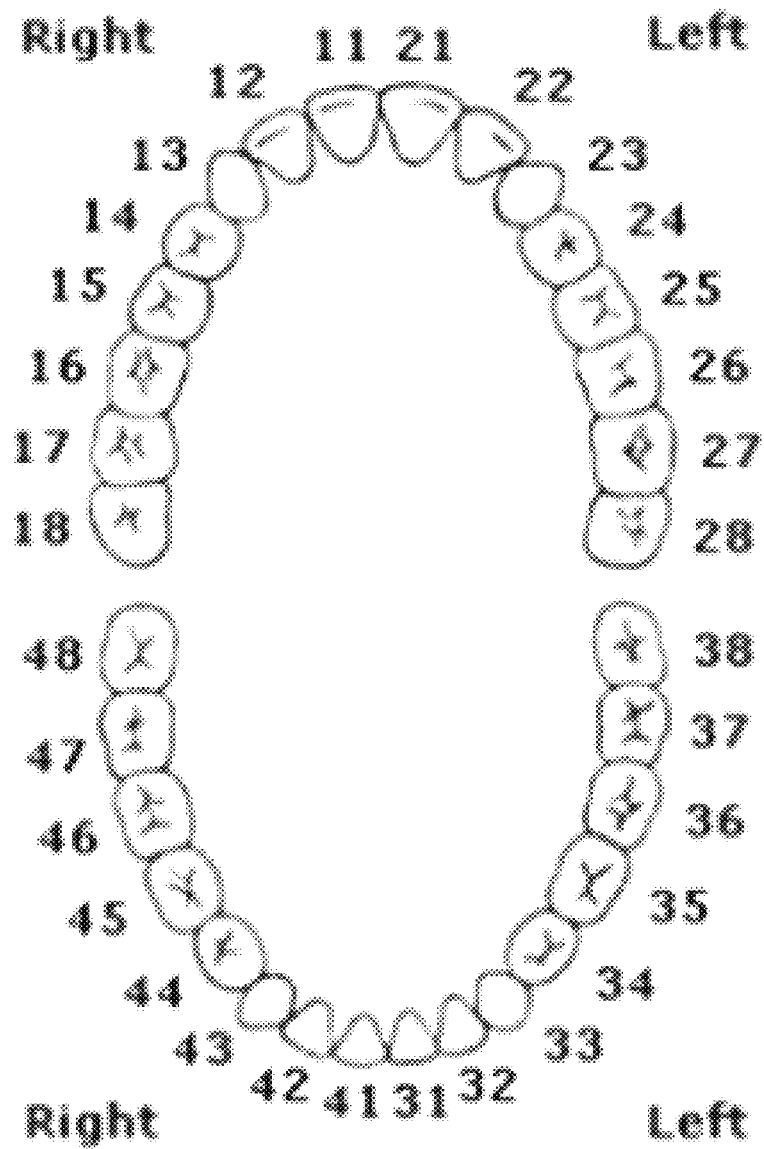
FIG. 2 is a diagram showing an example of teeth layout and numbering.

Referring to the teeth layout and numbering illustrated in FIG. 2, an example semantic class taxonomy for generating the SM can be as follows:

{"irrelevancy_mask", 0}, {"tongue", 1}, {"mouth_interior", 2}, {"gums_upper", 3}, {"gums_lower", 4}, {"tooth_11", 5}, {"tooth_12", 6}, {"tooth_13", 7}, {"tooth_14", 8}, {"tooth_15", 9}, {"tooth_16", 10}, {"tooth_21", 11}, {"tooth_22", 12}, {"tooth_23", 13}, {"tooth_24", 14}, {"tooth_25", 15}, {"tooth_26", 16}, {"tooth_31", 17}, {"tooth_32", 18}, {"tooth_33", 19}, {"tooth_34", 20}, {"tooth_35", 21}, {"tooth_36", 22}, {"tooth_41", 23}, {"tooth_42", 24}, {"tooth_43", 25}, {"tooth_44", 26}, {"tooth_45", 27}, {"tooth_46", 28}, {"unknown_object", 29}, {"implant", 30}

Where "unknown object" refers to any foreign object in the mouth that the system 100 cannot identify or is not interested in. "Implant" can refer to any exposed dental implant. In the above example, the actual number of classes is 31. In further examples, with the class labels extending all the way to the posterior molars, the number of classes can be 39; where teeth numbers 17, 18, 27, 28, 37, 38, 47, and 48 are included. In this example, the tooth numbering and names are derived from the FDI World Dental Federation notation.

Semantic categories generally belong to either particular anatomy in the mouth, or foreign objects (e.g., cotton, gauze, exposed implants, or dental tools) visible in some input images. The system 100 uniquely labels each tooth as a corresponding specific tooth under the FDI notation, rather than, for example, labeling them all as a generic class "tooth". The gums, tongue, and broad "mouth_interior" area can be labeled because they are used in synthesis to generate a plausible mouth. As described herein, for transformation simulation, the pixels of the image defining the interior of the mouth are replaced by the generated image, so the system 100 generates not only teeth but also other aspects of the mouth, such as gums, inner cheeks, and the like. As described herein, after transformation, the system 100 feeds into a synthesizer, so the system 100 learns a "B" label map that includes all possible classes in an ideal smile; including the shape of the gum tissue. In some cases, since exposed implants and foreign objects might appear in the input image, but may be generally undesirable in the simulated output image, these undesirable classes may be excluded from the output image.

In an example, training of the segmenter module 124 can include receiving training data comprising images with mouths and manually labelled categories for each such image. For a loss function, categorical cross entropy can be used for one-hot representations.

In some cases, aliasing in the segmentation map can cause issues and the use of soft semantics can help overcome such issues. Instead of having to learn and perform anti-aliasing approaches, which is not ideal, a semantically correct way to interpolate values is required. As an example, anti-aliasing an edge via a smudging technique, comprising taking an average on the order, may produce an incorrect result if the labels are stored as their direct value, as it is equivalent to hard semantics representation. For example, smudging of class 1 and class 11 would produce an average of class 6; which is completely incorrect as it produces a value for class 6, which is a different tooth altogether. In contrast, using one-hot encoding, the result of smudging is a vector (for example, [0.0, 0.5, . . . , 0.5, . . . 0.0]); which is a semantically correct representation of the border of two classes.

In a particular case, the segmenter module 124 uses a variant of the U-Net convolutional neural network (CNN) to build the SM; however, any suitable machine learning paradigm can be used. In this case, branches of the U-Net are determined along an ever decreasing resolution input image pyramid (for example, from top-to-bottom) and an ever increasing resolution pyramid of segmentation attempts (for example, from bottom-to-top). The output segmentation map can comprise the top, full resolution segmentation.

In another example, the segmenter module 124 can use a Mask R-CNN for segmentation. Mask R-CNN extends Faster Region-based CNN (R-CNN), which uses a Region Proposal Network (RPN). Faster R-CNN has two outputs for each candidate object, a class label and a bounding-box offset. Mask R-CNN adds another branch for outputting a prediction of segmentation masks on each Region of Interest (RoI) in parallel with an existing branch for classification and bounding box regression. The mask branch is a small Fully Convolutional Network (FCN) applied to each RoI, predicting a segmentation mask in a pixel-to-pixel manner.

Figure 3:
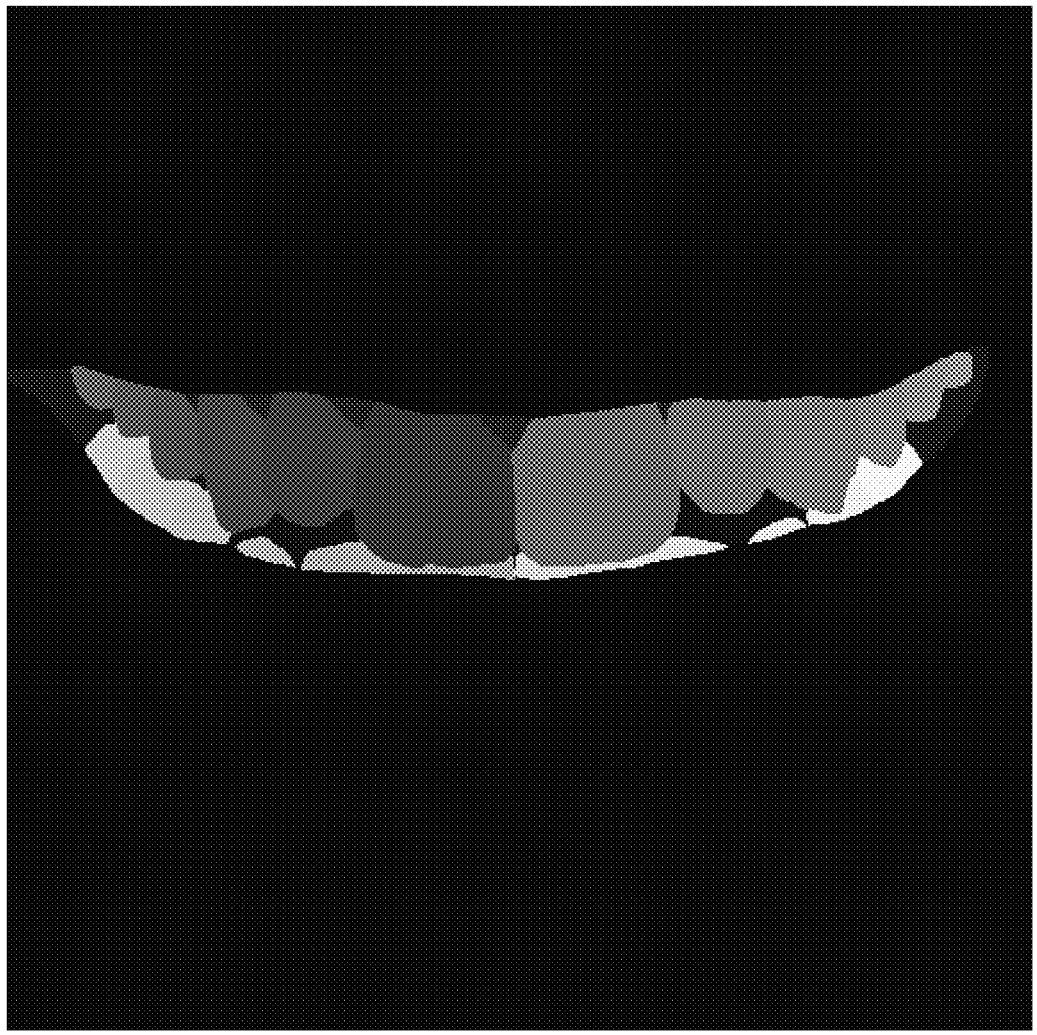
FIG. 3 is an example of an input segmentation map, in accordance with the system of FIG. 1.
Figure 4:
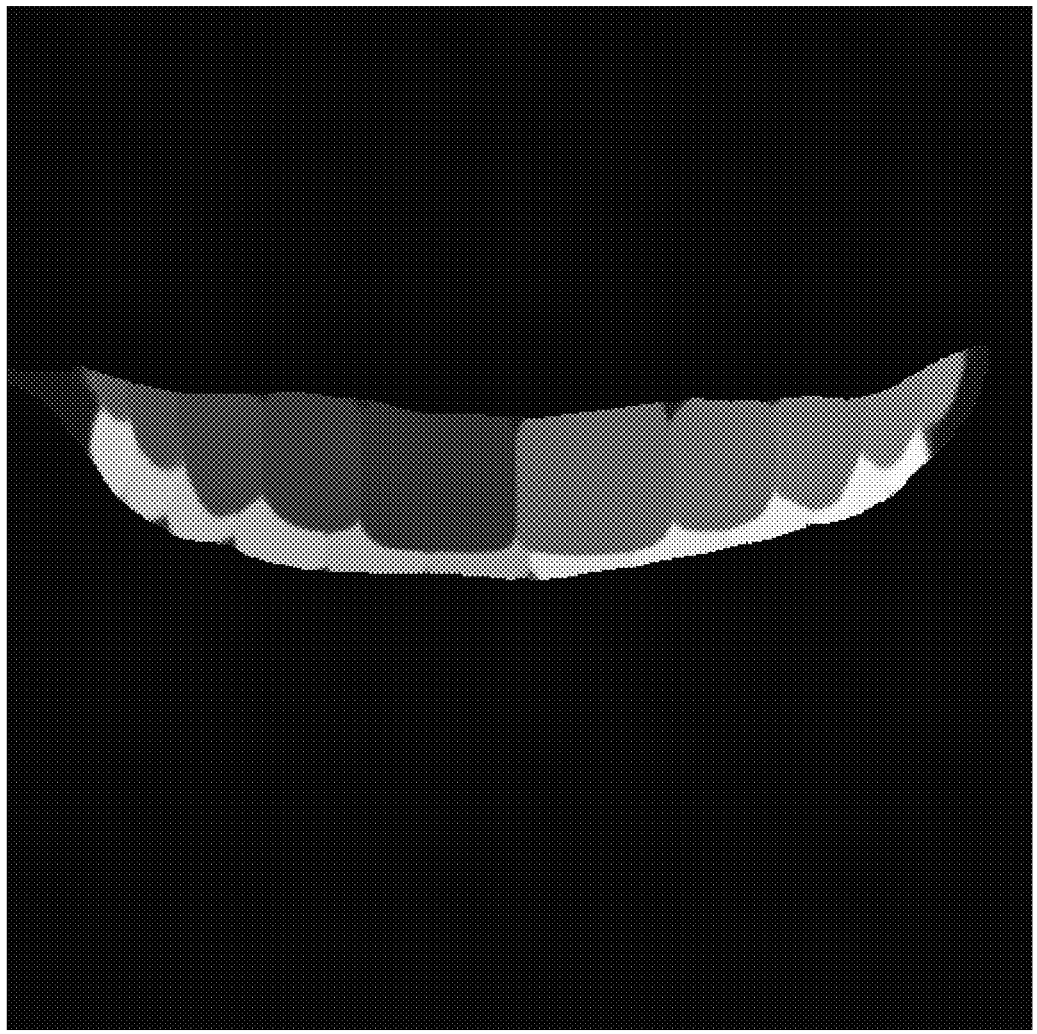
FIG. 4 is an example of an output segmentation map, in accordance with the system of FIG. 1.

The transformation module 122 takes as input the segmentation map produced by the segmenter module 124 (referred to as Segmentation A) and, via transformation, outputs an output segmentation map (referred to as Segmentation B) representing an idealized teeth layout. FIG. 3 illustrates an example of Segmentation A and FIG. 4 illustrates an example of a corresponding Segmentation B.

Figure 5:
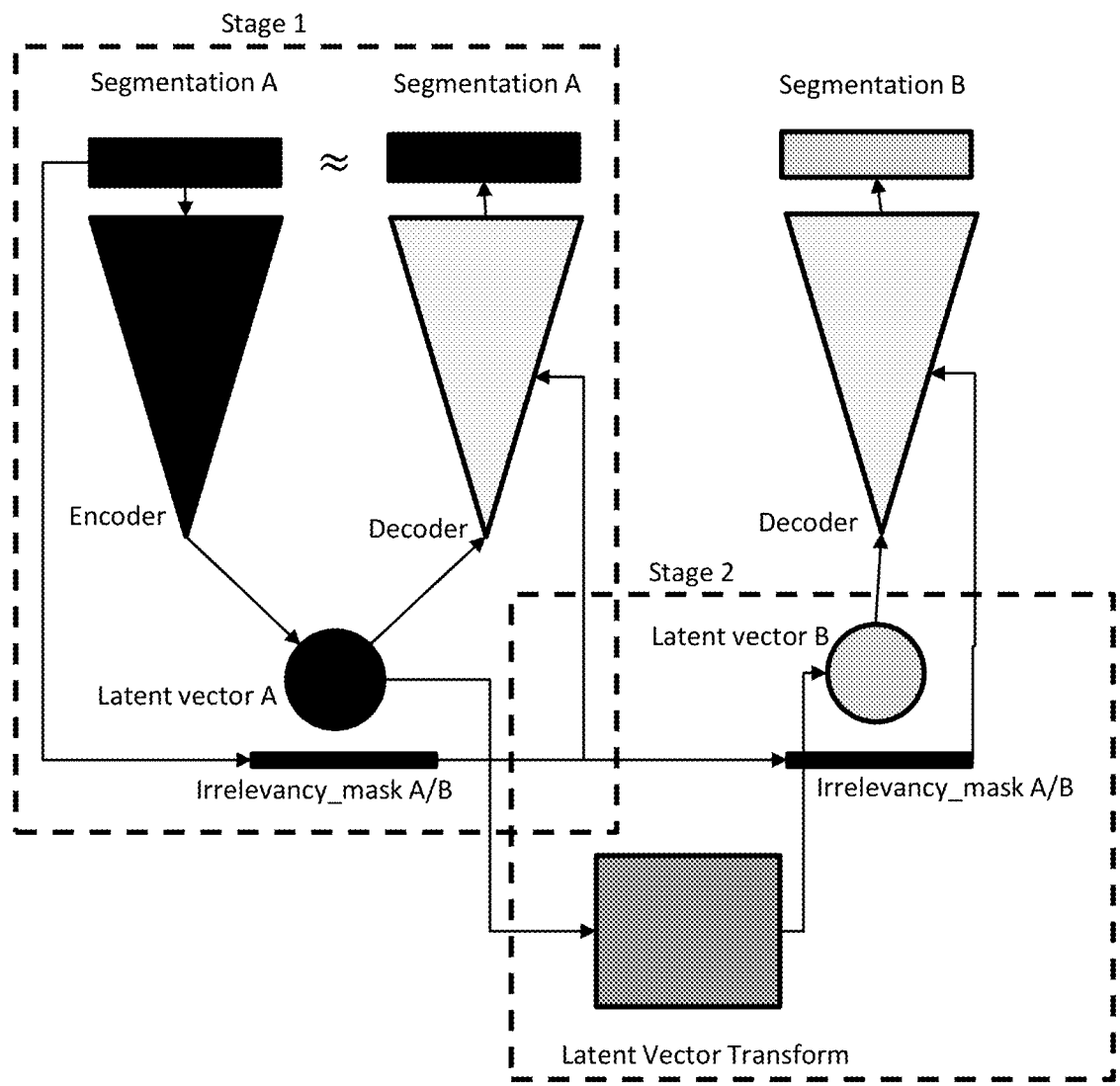
FIG. 5 is a diagram of an example architecture for a transformation module, in accordance with the system of FIG. 1.

In some cases, the system 100 can be implemented with pixel domain approaches, especially with network topologies that are inherently friendly to hierarchical representation, such as U-Net neural networks ["U-Net: Convolutional Networks for Biomedical Image Segmentation" by Olaf Ronneberger, Philipp Fischer and Thomas Brox accepted at MICCAI 2015]. In other cases, the system 100 can be implemented with the transformation carried out in a reduced dimensionality space. Such dimensionality reduction can be achieved, for example, via Principal Component Analysis. However, compression and reconstruction oriented approaches, or auto-encoders, can also reduce dimensionality. As illustrated in FIG. 5, a pair of networks, called an encoder and a decoder, can be used by the transformation module 122 to derive and reconstruct a latent vector representation (referred to as a "code"). The encoder is used for derivation (encoding) while the decoder is responsible for reconstruction of the segmentation map after compression (decoding). In an example, the code comprises an N-wide vector of [−1.0, 1.0] real numbers, where N can be any suitable vector length, matching our previous definition of one-hot encoding. Alternative categorical representations as listed previously are still a possibility.

The decoder can provide certain additional advantages. Since the transformation itself may not be observable by a user, the decoder can be used for verification purposes; i.e., whether the input, or something reasonably close to the input, can be reconstructed after encoding. Additionally, decoders can be used for interpretation of an output of a semantical (layout) transformation (as described herein).

The transformation module 122 can be trained using a set of training images of mouths with which SMs are generated by the segmenter module 124 and labelled by a user. In an example, the transformation module 122 can have a multi-layer-perceptron architecture; however, any suitable machine learning architecture can be used. In an example, the architecture can comprise a number (ex., 5-7) of expand then squeeze layers (ex., expanding to M wide and compressing back to P wide), each followed by LeakyRelu activations, except for the last layer, which is followed by a Tan H function to arrive at a [−1.0, 1.0] vector.

In some cases, the encoder can use a convolutional neural network (CNN) that, at every convolutional layer, reduces the tensor resolution 2×2 (going down from L×M initial image resolution) which progressively increases kernel depth (up to P); eventually reaching a vector of 1×1×P, which is the size of the latent vector (wherein "P" is a dimension count of the input latent vector). In this way, there is two-dimensional instance normalization and spectral normalization of the convolutional kernels. As described above, activations are Leaky ReLUs except for after the last convolutional layer where the activation is Tan H to accommodate the desired type of latent vector.

In some cases, the decoder can be structurally the inverse of the encoder, going up from the 1×1×P vector to the L×M×31 SM; using the same kind of activations and normalizations. In some cases, a learnable denormalization can be used after the two-dimensional instance normalization to allow the system 100 to not always revert to a unit norm, but rather allow for learning and normalizing into more useful distributions. Otherwise, there may be an issue of trying to find meaningful distributions out of previously normalized values.

As shown in FIG. 5, the encoder and the decoder use the irrelevancy mask. Usually, the input images are images of the mouth area with teeth exposed (such as a cropped image of a smile). Some of the pixels of the input image are outside the intraoral region. The irrelevancy mask (often represented via semantical category 0) is then used to signify these areas outside the intraoral region. In some cases, the system 100 operates on (S-1) semantical categories, where the irrelevancy mask (e.g. semantical category 0) is exempt from processing and its path bypasses most of the network as illustrated, leaving it unchanged. In some cases, despite being immutable, the irrelevancy map is still provided as an input to system 100 as additional information about the location and shape of the mouth boundary. Ultimately this design is a manifestation of the practical principle, that any new synthetic imagery must fit into the intraoral region of the original input image.

The segmenter module 124 can determine which pixels to include in the irrelevancy mask. The segmenter module 124 uses a trained artificial neural network, as described herein, trained with training images labelled with all intraoral anatomy and applicable semantic categories, to determine which pixels are outside the intraoral region (lip boundary). In some cases, the segmenter module 124 can operate on an image pyramid (a stack of images that is a product of recursive 2×2 down-sampling). In this way, the segmenter module 124 starts at the bottom image of least resolution and traverses to the top image of highest resolution. This implementation of the segmenter module 124 supports segmentation that is initially object based (given that low-resolution images can capture object locations accurately, but not their shape) and it is gradually refined via the local information available at higher resolutions.

In an embodiment, as illustrated in FIG. 5, training of the system 100 can comprise two separate stages (stage 1 and stage 2). In stage 1, the transformation module 122 trains the encoder and the decoder, where the goal of such training is to determine whether the output of the decoder is as close as possible to the input segmentation map. Additional constraints to offer improved conditioning of the learning problem may also be supplemented here as appropriate. In stage 2, the transformation module 122 trains a transformer network to transform latent vector A into latent vector B. Comparatively, this is generally a faster process that usually has earlier convergence. During stage 2, the results of the first stage remain constant, and the transformer network does not feed back. The transformer network can be trained with a training dataset of images of before and after dental transformation. The 'before' training images are converted to Segmentation Map A and then encoded to latent vector A, while the 'after' training images are converted to Segmentation Map B and encoded to latent vector B. The transformer learns a transformation of latent vector A to latent vector B. Then the decoder is used to transform it back to a Segmentation Map B from the latent vector. The learning paradigm can use any suitable approach, for example, stochastic gradient descent.

Figure 6:
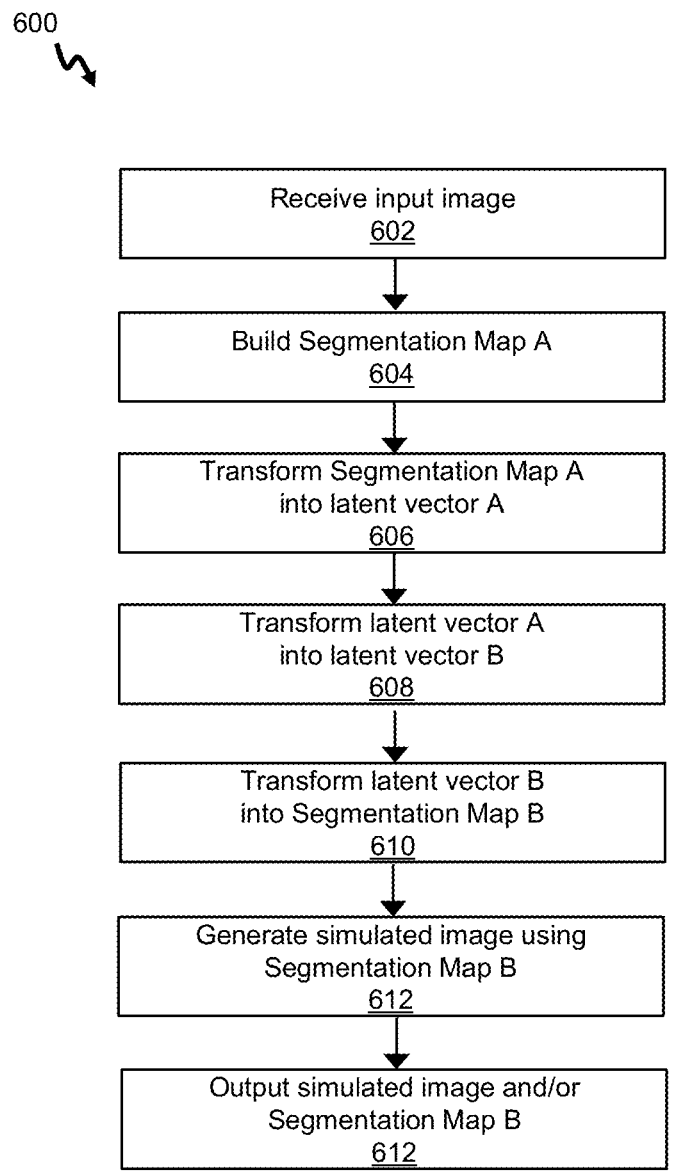
FIG. 6 is a flow chart of a method for image synthesis of dental anatomy transformation, in accordance with an embodiment.

FIG. 6 is a flowchart illustrating an embodiment of a method 600 for image synthesis of dental anatomy transformation. At block 602, the input module 120 receives an input image; for example, received from the user interface 106, from the network interface 108, or from the database 116. The input image comprising a mouth with teeth exposed.

At block 604, the segmenter module 124 builds an input segmentation map (Segmentation Map A) using the input image as input; for example, using a trained U-Net convolutional artificial neural network.

At block 606, the transformation module 122 uses a trained encoder to transform the input segmentation map into an input latent vector (latent vector A). At block 608, the transformation module 122 uses a trained transformer network to transform the input latent vector to an output latent vector (latent vector B).

At block 610, the transformation module 122 transforms the output latent vector into an output segmentation map (Segmentation Map B).

At block 612, the synthesis module 128 generates a simulated image comprising the mouth using the output segmentation map (Segmentation Map B).

At block 614, the output module 126 outputs the simulated image, the output segmentation map, or both, to the user interface 106, to the network interface 108, or to the database 116.

The synthesis module 128 generates the simulated image by taking as input the output segmentation map, and the input image. In some cases, the simulated image can include stylistic aspects of the input image by retaining some characteristics; for example, colour of the teeth in the input image. In an example, for retaining the stylistic aspects, the transformation module 122 can use a statistical encoder to encode style into a latent vector. Once the style is encoded, the synthesis module 128 can generate the simulated image; for example, by "in-painting" parts of the semantical map. In some cases, a bottom-to-top scheme can be used to gradually increase the resolution of the simulated image.

In some cases, the transformation module 122 uses a regularized auto-encoder (RAE), in order to achieve strong regularization, for the encoder and the decoder. While Variational Auto-Encoders (VAE) can be used, RAE is preferable because it incorporates elements of strong regularizations (e.g., spectral normalization) on the decoder but not on the encoder. In some cases, similarity between the input of the encoder and the output of the decoder can be determined by a fixed metric (e.g., L1 distance), and in some cases, application of an adversarial discriminator may also be beneficial. The adversarial discriminator can be similar to the encoder, except that it has an output of 1×1×1 due to being a loss function implementing the adversarial approach.

In some cases, an additional constraint can be applied by enforcing the encoder to have maximal information/entropy via maximum variety of instances of code within batches. This can be used to resist mode-collapse. In this way, the system 100 can enforce the compressed codes to have maximum entropy. Intuitively, if they do not have maximum entropy, that would mean they could be further compressed, which would contradict the nature of compression relying on the minimum amount of entropy needed.

The synthesis module 128 generates the synthesized image using any suitable machine learning approach; for example, synthesizing a photo-realistic simulated image from SMs using conditional generative adversarial networks (conditional GANs). Generally, GANs aim to model a natural image distribution relative to an input SM by training under the constraint that generated samples ideally strive to be indistinguishable from natural images; for example, using a coarse-to-fine generator, a multi-scale discriminator (attempting to determine whether the generated samples are distinguishable from original ones), and a robust adversarial learning objective function (commanding the training of both the generator and the discriminator). In a particular case, as described by Wang et al. ("High-Resolution Image Synthesis and Semantic Manipulation with Conditional GANs," in Proc. IEEE Conf. Comput. Vis. Pattern Recognit. (CVPR), June 2018., pp. 8798-8807), the conditional GANs may be used for generation, accumulating global distributions, and local refinements that are defined relative to global statistics. The multi-scale discriminator comprises a plurality of single-scale discriminators having identical or similar structures but operating at different image scales; where under different image scales is understood to mean different resolution versions of the same image.

For GANs, the encoder, the generator, and the discriminator can be trained in tandem, solving a minimax problem. For the training of the generator, one or more of, for example, hinge loss, feature loss (ex., L1 distance on intermediate features), and perceptual losses from a VGGNet, can be used. For the encoder, for example, Kullback-Leibler divergence loss can be used to regulate entropy. For the training of the discriminator, for example, hinge loss can be used, amongst other suitable candidates like Wasserstein loss (also known as earth mover's distance), or other bounded loss functions such as, for example, sigmoid or Tan H as used for adversarial networks.

In other examples, the synthesis module 128 can use modified perceptual loss to synthesize the simulated image.

Advantageously, in some cases, the system 100 can use cycle consistency in the context of the encoder and decoder. In these cases, the transformation module 122 can encode the SMs, decode, and then once again encode the decoded data to determine the difference between the originally encoded data and the later encoded data. The difference between the two can be determined using a real distance function. Ideally, this encoded data would be the same as the originally encoded data (if there was lossless compression). Having this additional constraint can be used to ensure that the small perturbations of compression loss are defined in such way that its impact in the latent space is minimal. This is also useful for enforcing that similar segmentation maps should have similar codes, which is a very useful property for conditioning. Advantageously, the encoder would otherwise only receive gradients via the decoder during training, but this approach establishes another source of gradients. It is also advantageous for regularization because the imperfections of the decoder ensure small perturbations in the close vicinity of a training sample.

While the present embodiments provide certain approaches with respect to machine learning, other approaches can be used. For example, U-Net designs whereby the encoder and the decoder are implemented together (downwards branch as encoder, upwards branch as decoder). In another example, other GAN topologies can be used, for example, DCGANs ["Unsupervised Representation Learning with Deep Convolutional Generative Adversarial Networks" by Alec Radford, Luke Metz, Soumith Chintala, ICLR 2016].

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A method for image synthesis of dental anatomy transformation, comprising:
generating, from an input image, an input latent vector, wherein the input image comprises a plurality of pixels and at least a subset of pixels, of the plurality of pixels, corresponds to one or more exposed teeth in a subject's intraoral region, wherein generating of the input latent vector comprises:
analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label; and
encoding, using a trained encoder model, the input segmentation map to generate the input latent vector, wherein the input latent vector is a compressed representation of the input segmentation map;
transforming, using a trained transform model, the input latent vector into an output latent vector;
decoding, using a trained decoder, the output latent vector to generate an output segmentation map, the output segmentation map comprising a transformed semantic representation comprising, for one or more teeth, one or more respective transformed groups of pixels; and
synthesizing, using a trained synthesis model, the output segmentation map to generate an output simulated image that displays the subject's intraoral region including simulated teeth having the one or more respective transformed groups of pixels.

2. The method of claim 1, further comprising:
generating an output including one or more of the output segmentation map and the output simulated image.

3. The method of claim 1, wherein the teeth, expressed by respective transformed group of pixels, have one or more of a transformed position, transformed orientation or transformed shape.

4. The method of claim 1, wherein,
a segment of the plurality of pixels, in the input image, corresponds to a region outside of the subject's intraoral region, and
analyzing the plurality of pixels to generate the input segmentation map further comprises assigning the segment of pixels to an irrelevancy mask, and
the segment of pixels assigned to the irrelevancy mask are excluded from the encoding, transforming and decoding and are included in the output segmentation map to define the location and shape of the intraoral region.

5. The method of claim 1, wherein the trained encoder and trained decoder comprise an auto-encoder.

6. The method of claim 1, further comprising training an encoder and a decoder to generate the trained encoder and the trained decoder by:
receiving a first segmentation map;
encoding, using the encoder, the first segmentation map to generate a latent vector;
decoding, using the decoder, the latent vector to generate a second segmentation map;
determining a loss function associated with a difference between the first and second segmentation maps; and
using the loss function to train the autoencoder.

7. The method of claim 1, wherein each of the trained encoder and trained decoder use a multi-layer perceptron architecture, and wherein the multi-layer-perceptron architecture for the trained encoder can comprise a plurality of expand then squeeze layers each followed by a LeakyRelu activation except for a last layer that is followed by a Tan H function to accommodate for a desired type of latent vector.

8. The method of claim 1, wherein the trained encoder and trained decoder use a convolution neural network (CNN), wherein for the trained encoder, the activation functions comprise LeakyRelu activation except for a last convolution layer that is followed by a Tan H function.

9. The method of claim 1, wherein,
the trained encoder converts the input segmentation map of dimensions L×M×S into the input latent vector of dimensions 1×1×P, wherein "P" is a dimension count of the input latent vector, "L" and "M" are the dimensions of the input image, and "S" is the number of semantic categories, and
the input latent vector defines an input tensor, and at one or more layers of the CNN, a resolution of the input tensor is reduced by a factor of 2×2 while concurrently doubling a number of kernels up to "P" kernels to generate the input latent vector of dimensions 1×1×P, and
the trained decoder has an inverse structure to the trained encoder and converts the output latent vector having dimensions of 1×1×P to the output segmentation map having dimensions of L×M×S.

10. The method of claim 1, wherein the trained synthesis model comprises a trained conditional generative adversarial network (GAN), the conditional GAN comprises one or more of an encoder, a coarse-to-fine generator, a multi-scale discriminator and a robust adversarial learning objective function and the multi-scale discriminator comprises a plurality of single-scale discriminators having identical or similar structure but operate at different image scales comprising different resolution versions of a same image.

11. The method of claim 1, wherein transforming the input latent vector into the output latent vector further comprises the trained transform model inserting a representation of one or more simulated teeth in the output latent vector.

12. A system for image synthesis of dental anatomy transformation, comprising:
a memory unit for storing an input image, wherein the input image comprises a plurality of pixels and at least a subset of pixels, of the plurality of pixels, corresponds to one or more exposed teeth in a subject's intraoral region;
a processing unit coupled to the memory unit and being operable to perform a method comprising:
generating, from the input image, an input latent vector, wherein generating of the input latent vector comprises:

analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label;

encoding, using a trained encoder model, the input segmentation map to generate the input latent vector, wherein the input latent vector is a compressed representation of the input segmentation map;

transforming, using a trained transform model, the input latent vector into an output latent vector;

decoding, using a trained decoder, the output latent vector to generate an output segmentation map, the output segmentation map comprising a transformed semantic representation comprising, for one or more teeth, one or more respective transformed pixels; and synthesizing, using a trained synthesis model, the output segmentation map to generate an output simulated image that displays the subject's intraoral region including simulated teeth having the one or more respective transformed groups of pixels.

13. The system of claim 12, the processing unit being further operable to preform the method comprising:
generating an output including one or more of the output segmentation map and the output simulated image.

14. The system of claim 12, wherein the teeth, expressed by respective transformed group of pixels, have one or more of a transformed position, transformed orientation or transformed shape.

15. The system of claim 12, wherein,
a segment of the plurality of pixels, in the input image, corresponds to a region outside of the subject's intraoral region, and
analyzing the plurality of pixels to generate the input segmentation map further comprises assigning the segment of pixels to an irrelevancy mask, and
the segment of pixels assigned to the irrelevancy mask are excluded from the encoding, transforming and decoding and are included in the output segmentation map to define the location and shape of the intraoral region.

16. The system of claim 12, wherein the trained encoder and trained decoder comprise an auto-encoder.

17. The system of claim 12, the processing unit being further operable to preform training of an encoder and a decoder to generate the trained encoder and the trained decoder by:
receiving a first segmentation map;
encoding, using the encoder, the first segmentation map to generate a latent vector;
decoding, using the decoder, the latent vector to generate a second segmentation map;
determining a loss function associated with a difference between the first and second segmentation maps; and
using the loss function to train the autoencoder.

18. The system of claim 12, wherein each of the trained encoder and trained decoder use a multi-layer perceptron architecture, and wherein the multi-layer-perceptron architecture for the trained encoder can comprise a plurality of expand then squeeze layers each followed by a LeakyRelu activation except for a last layer that is followed by a Tan H function to accommodate for a desired type of latent vector.

19. The system of claim 12, wherein the trained encoder and trained decoder use a convolution neural network (CNN), wherein for the trained encoder, the activation functions comprise LeakyRelu activation except for a last convolution layer that is followed by a Tan H function.

20. The system of claim 12, wherein,
the trained encoder converts the input segmentation map of dimensions L×M×S into the input latent vector of dimensions 1×1×P, wherein "P" is a dimension count of the input latent vector, "L" and "M" are the dimensions of the input image, and S is the number of semantic categories, and
the input latent vector defines an input tensor, and at one or more layers of the CNN, a resolution of the input tensor is reduced by a factor of 2×2 while concurrently doubling a number of kernels up to "P" kernels to generate the input latent vector of dimensions 1×1×P, and
the trained decoder has an inverse structure to the trained encoder and converts the output latent vector having dimensions of 1×1×P to the output segmentation map having dimensions of L×M×S.

21. The system of claim 12, wherein the trained synthesis model comprises a trained conditional generative adversarial network (GAN), the conditional GAN comprises one or more of an encoder, a coarse-to-fine generator, a multi-scale discriminator and a robust adversarial learning objective function and the multi-scale discriminator comprises a plurality of single-scale discriminators having identical or similar structure but operate at different image scales comprising different resolution versions of a same image.

22. The system of claim 12, wherein transforming the input latent vector into the output latent vector further comprises the trained transform model inserting a representation of one or more simulated teeth in the output latent vector.

23. A non-transitory computer-readable medium storing computer program instructions which, when executed by a computer processor, cause the computer processor to perform a method for image synthesis of dental anatomy transformation, the method comprising:
generating, from an input image, an input latent vector, wherein the input image comprises a plurality of pixels and at least a subset of pixels, of the plurality of pixels, corresponds to one or more exposed teeth in a subject's intraoral region, wherein generating of the input latent vector comprises:
analyzing, using a trained segmentation model, the plurality of pixels to generate an input segmentation map, the input segmentation map comprising a semantic representation of the subject's intraoral region, wherein in the semantic representation, each tooth in the intraoral region is represented by a group of pixels and associated with a respective categorical label; and
encoding, using a trained encoder model, the input segmentation map to generate the input latent vector, wherein the input latent vector is a compressed representation of the input segmentation map;
transforming, using a trained transform model, the input latent vector into an output latent vector;
decoding, using a trained decoder, the output latent vector to generate an output segmentation map, the output segmentation map comprising a transformed semantic representation comprising, for one or more teeth, one or more respective transformed groups of pixels; and synthesizing, using a trained synthesis model, the output segmentation map to generate an output simulated image that displays the subject's intraoral region including simulated teeth having the one or more respective transformed groups of pixels.

* * * * *